United States Patent [19]

Patel

[11] 4,143,651
[45] Mar. 13, 1979

[54] CATHETER

[75] Inventor: Bhupendra C. Patel, Elgin, Ill.

[73] Assignee: The Kendall Company, Boston, Mass.

[21] Appl. No.: 848,169

[22] Filed: Nov. 3, 1977

[51] Int. Cl.² ............................................. A61M 25/00
[52] U.S. Cl. .................................. 128/349 B; 128/246
[58] Field of Search ........ 128/349 R, 349 B, 349 BV, 128/348, 350 R, 351, 246, 344

[56] References Cited

U.S. PATENT DOCUMENTS

| 3,634,924 | 1/1972 | Blake et al. | 128/349 B X |
| 3,736,939 | 6/1973 | Taylor | 128/349 B |
| 3,832,253 | 8/1974 | Palma et al. | 128/349 BV |
| 4,026,296 | 5/1977 | Stoy et al. | 128/349 B |
| 4,055,187 | 10/1977 | Patel et al. | 128/349 B |

FOREIGN PATENT DOCUMENTS 1436679  5/1976  United Kingdom ................ 128/349 B Primary Examiner—E. H. Eickholt
Attorney, Agent, or Firm—Powell L. Sprunger

[57] ABSTRACT

A catheter comprising, an elongated inner first tube defining a main lumen, an elongated annular sleeve of elastic material covering a longitudinal portion of the first tube, and an elongated outer second tube covering a longitudinal portion of the sleeve and having a distal end proximally spaced from a distal end of the sleeve. The catheter has a tip secured to a distal end of the first tube and having a proximally extending annular flange covering the distal end of the sleeve, with the distal end of the second tube being spaced from the flange to define an inflatable segment of the sleeve intermediate the distal end of the second tube and the flange.

22 Claims, 4 Drawing Figures

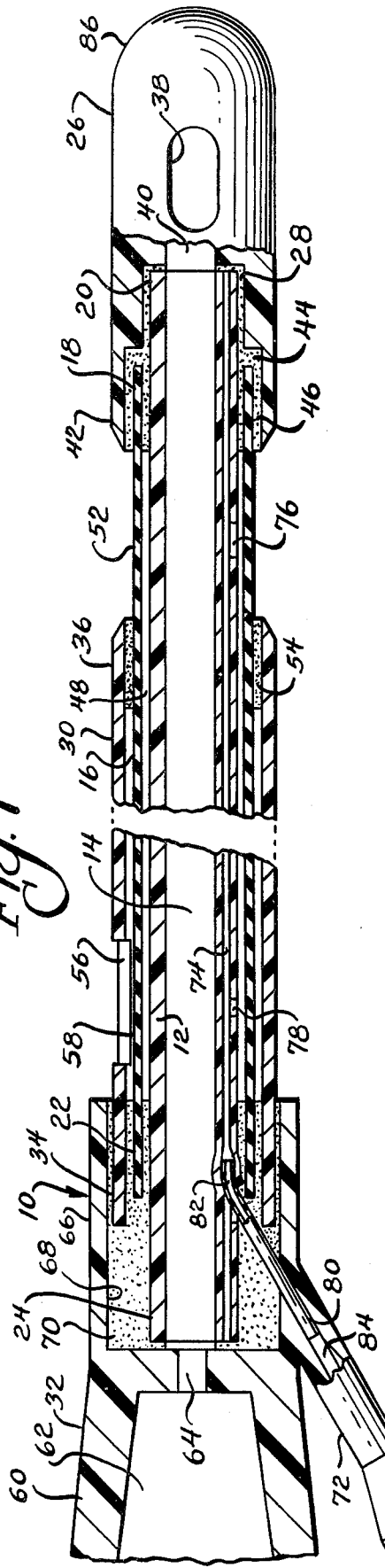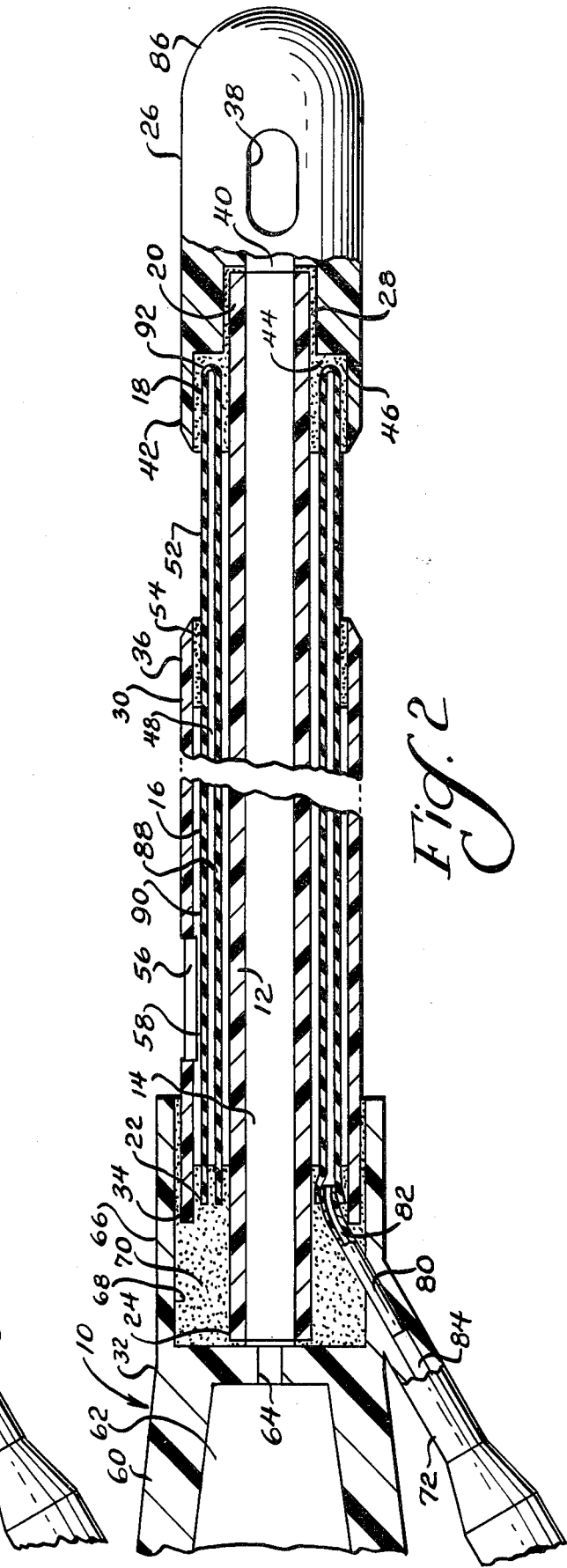

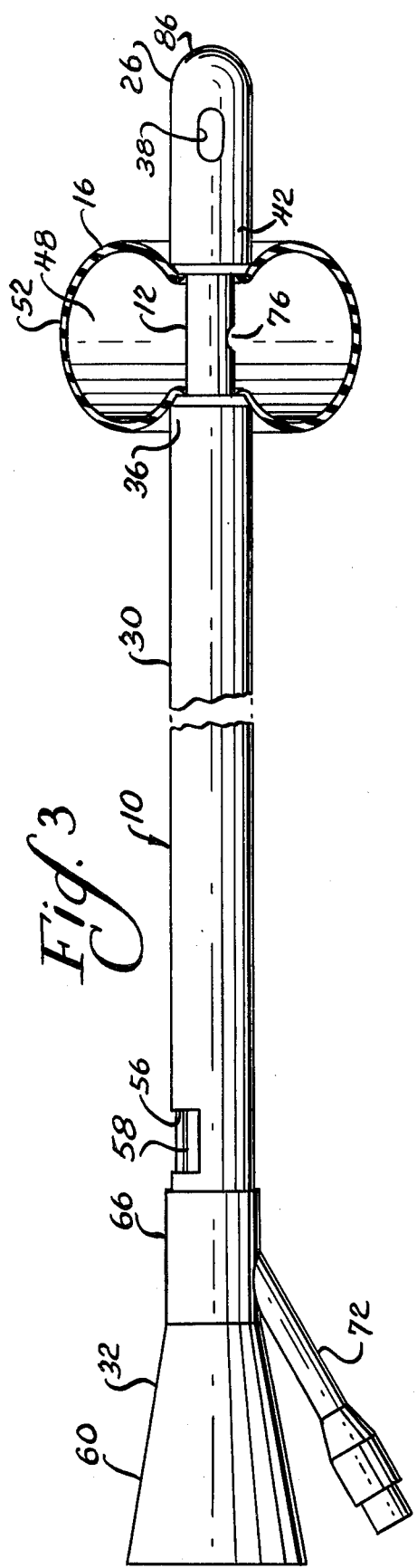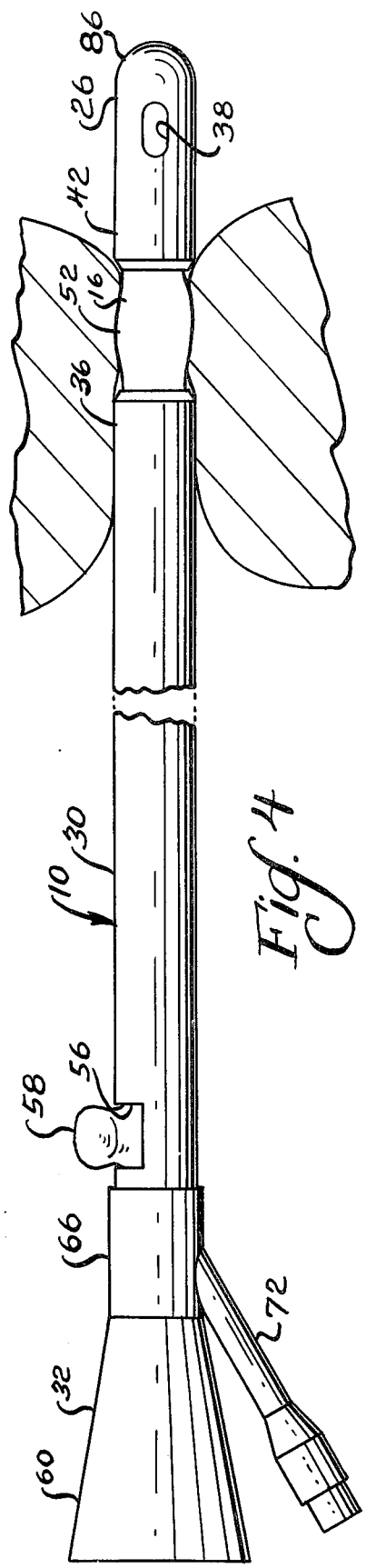

CATHETER

BACKGROUND OF THE INVENTION

The present invention relates to catheters, and more particularly to inflatable balloons for such catheters.

In the past, a various assortment of catheters, such as Foley catheters and endotracheal tubes, have been proposed for use in patients. In the case of urinary catheters, a conventional Foley catheter is normally constructed having a shaft defining a drainage lumen extending from a drainage eye adjacent a distal end of the shaft and an inflation lumen in the wall of the shaft, and having an expansible balloon overlying a distal portion of the shaft and defining a cavity communicating with the inflation lumen. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

A great majority of Foley catheters have been made from latex rubber through dipping techniques known to the art. However, a number of problems have been encountered with conventional latex catheters, such as difficulties in manufacture and delamination of the catheter sidewalls causing blockage in the inflation lumen. Accordingly, there has been a desire to construct catheters from materials which display superior properties both from the view of improved performance during use and permitting simplified manufacture to reduce cost. For example, it is preferred that the catheter shaft be made from a material which can be extruded in order to facilitate the manufacturing process and eliminate the delamination problems associated with dipped latex catheters. Additionally, the materials of the catheter shaft must be compatible with the patient's body to prevent deleterious results during use. The shaft, although flexible, should also have sufficient rigidity to permit placement of the catheter and prevent collapse of the shaft side walls. The balloon, of course, should be flexible and elastic to permit inflation in the patient's bladder, and preferably has a sufficient memory to assume its initial deflated configuration against the catheter shaft while being removed from the patient.

Unfortunately, many of the materials which display excellent properties when used for the catheter shaft are not suitable as a balloon, and vice versa. Hence, in many cases it is necessary to use dissimilar materials for the balloon and shaft which has created serious difficulties in joining the balloon and shaft together. Although it is often relatively simple to obtain a satisfactory bond between the balloon and shaft when the same material is used for both, known bonding techniques such as adhesive or heat sealing often do not provide sufficient strength between the balloon and shaft when dissimilar materials are used. For example, porous polytetrafluoroethylene provides an excellent candidate for the catheter shaft, but has been found unsatisfactory as the catheter balloon. Accordingly, attempts have been made to bond balloons made of suitable materials, such as silicone and latex, to such a shaft, and satisfactory bonds are only obtained with extreme difficulty which unduly complicates manufacture of the catheters.

SUMMARY OF THE INVENTION

A principal feature of the present invention is the provision of a catheter of simplified construction having an improved balloon.

The catheter of the present invention comprises, an elongated inner first tube defining a main lumen, an elongated annular sleeve of elastic material covering a longitudinal portion of the first tube, and an elongated outer second tube covering a longitudinal portion of the sleeve and having a distal end proximally spaced from a distal end of the sleeve. The catheter has a tip secured to a distal end of the first tube and having a proximally extending annular flange covering the distal end of the sleeve, with the distal end of the second tube being spaced from the flange to define an inflatable segment of the sleeve intermediate the distal end of the second tube and the flange. The catheter has means for establishing communication with the inflatable sleeve segment.

A feature of the present invention is that the sleeve is retained between the first tube and the tip and second tube in order to firmly anchor the sleeve in place.

Another feature of the invention is that the catheter may be constructed in a simplified manner and at a reduced cost.

Yet another feature of the invention is that dissimilar materials may be used for the sleeve and the catheter tubes and tip resulting in a catheter of improved characteristics.

A feature of the invention is that the sleeve may be inflated intermediate the distal end of the second tube and the tip flange.

A further feature of the invention is that the second tube may have an opening overlying a portion of the sleeve and located proximal the sleeve segment to permit inflation of the sleeve portion through the opening when the sleeve segment is obstructed.

Thus, another feature of the invention is that the catheter provides a safety device to relieve pressure from the sleeve segment when it is obstructed.

Still another feature of the invention is that the sleeve may have inner and outer walls which define a cavity communicating with the sleeve segment.

Further features will become more fully apparent in the following description of the embodiments of this invention and from the appended claims.

DESCRIPTION OF THE DRAWINGS

In the drawings:

FIG. 1 is a fragmentary elevational view, taken partly in section, of a catheter of the present invention;

FIG. 2 is a fragmentary elevational view, taken partly in section, of another embodiment of the catheter of the present invention;

FIG. 3 is a fragmentary elevational view, taken partly in section, of the catheter of the present invention showing a sleeve segment of the catheter as inflated; and FIG. 4 is a fragmentary elevational view of the catheter of the present invention illustrating activation of a safety device when the sleeve segment is obstructed.

DESCRIPTION OF THE PREFERRED EMBODIMENTS

Referring now to FIG. 1, there is shown a urinary catheter generally designated 10 for draining urine from the bladder of a patient. Although, for convenience, the present invention will be described in connection with a urinary catheter, it will be understood that the principals of the present invention are equally applicable to other suitable catheters, such as endotracheal tubes. The catheter 10 has an elongated inner first tube 12 defining a main drainage lumen 14 of the catheter 10. The catheter 10 has an elongated annular sleeve 16 of elastic material which covers a longitudinal portion of the first tube 12, and which may extend substantially the length of the first tube 12, as shown, although a distal end 18 of the sleeve 16 may be spaced from a distal end 20 of the first tube 12, and a proximal end 22 of the sleeve 16 may be spaced from a proximal end 24 of the first tube 12. The catheter 10 has a tip 26 secured to the distal end 20 of the first tube 12, with the tip 26 having an annular recess 28 to receive the distal end 20 of the first tube 12. The catheter 10 has an elongated second outer tube 30 covering a longitudinal portion of the sleeve 16. Also, the catheter 10 has a connector 32 secured to the proximal end 24 of the first tube 12 and a proximal end 34 of the second tube 30.

As shown, the tip 26 has at least one opening or drainage eye 38 and a lumen 40 communicating with the drainage lumen 14 of the first tube 12. Also, the tip 26 has a proximally extending annular flange 42 defining an annular recess 44 to receive the distal end 18 of the sleeve 16. The distal end 18 of the sleeve 16 may be bonded to the flange 42 and the outer surface of the first tube 12 by suitable means 46, such as adhesive, in order to secure the distal end 18 of the sleeve 16 in place and close a distal end of a cavity 48 intermediate the sleeve 16 and first tube 12. In addition, the bonding means 46 may be utilized to secure the tip 26 to the distal end 20 of the first tube 12 in the recess 28. In this manner, the tip 26, first tube 12, and distal end 18 of the sleeve 16 are secured together by the bonding means 46.

As shown, the distal end 36 of the second tube 30 is spaced proximally from the tip flange 42 in order to define an inflatable segment 52 of the sleeve 16 located intermediate the distal end 36 of the second tube 30 and the tip flange 42. If desired, the distal end 36 of the second tube 30 may be secured to the sleeve 16 in a circumferential zone by suitable bonding means 54, such as adhesive. The second tube 30 also has an opening 56 overlying a portion 58 of the sleeve 16 located proximal the sleeve segment 52 for a purpose which will be described below.

The connector 32 has a funnel portion 60 having a cavity 62 for connection to a drainage tube (not shown), and an opening or lumen 64 communicating between the cavity 62 and the main lumen 14 of the first tube 12. Also, the connector 32 has a distally extending annular flange 66 defining a bore 68. As shown, the flange 66 covers the proximal end 34 of the second tube 30, and overlies the proximal end 22 of the sleeve 16 and the proximal end 24 of the first tube 12. The proximal ends of the first tube 12, the sleeve, 16, and the second tube 30 may be bonded to the connector flange 66 by suitable means 70, such as adhesive, in order to secure these parts of the catheter together and close the proximal end of the cavity 48 intermediate the sleeve 16 and first tube 12. The connector 32 also has a side arm 72 with suitable valve means (not shown) of known type for use in inflating the sleeve segment 52.

The first tube 12 has an inflation lumen 74 in the wall of the first tube 12 and communicating with the cavity 48 through an opening 76 located beneath the sleeve segment 52. In addition, the first tube 12 has an aperture 78 communicating with the inflation lumen 74 in order to inflate the sleeve portion 58 under specified conditions. Of course, if desired, the opening 56 of the second tube 30 may overlie the aperture 78 of the first tube 12 in order to establish direct communication between the inflation lumen 74 and the portion of the cavity 48 beneath the opening 56. In fact, the opening 56 may be defined by spaced sections of the outer tube 30 in the catheter, as desired. The catheter 10 also has a tubular segment 80 having a lumen 82 communicating between a lumen 84 in the side arm 72 and the inflation lumen 74 in the first tube 12. In this manner, communication is established between the side arm 72 and the cavity 48 beneath the sleeve segment 52 through the tube 80, the inflation lumen 74, and the opening 76.

In use, a distal end 86 of the catheter 10 defined by the tip 26 is passed through the patient's urethra until the tip 26 and balloon segment 52 are located in the patient's bladder. With reference to FIGS. 1 and 3, a syringe (not shown) is connected to the side arm 72 in order to open the valve means and pump fluid through the inflation lumen 74 into the portion of the cavity 48 beneath the balloon segment 52. Thus, with reference to FIG. 3, the balloon segment 52 located intermediate the second tube 30 and the tip 26 inflates in the bladder, such that the sleeve segment 52 serves as an inflatable balloon to retain the catheter in place in the patient. However, with reference to FIGS. 1 and 4, in the event that the sleeve segment 52 should be obstructed, the sleeve portion 58 inflates through the opening 56 in order to relieve pressure beneath the sleeve segment 52. Thus, in the event that the sleeve segment 52 is inadvertently positioned in the patient's urethra during inflation, the sleeve portion 58 inflates in order to prevent inflation of the sleeve segment 52 and possible harm to the patient.

Thus, it will be apparent that the catheter of the present invention may be made in a simplified manner through use of the inner tube 12, the sleeve 16, the outer tube 30, the tip 26, and the connector 32. In a preferred form, the first tube 12 and the second tube 30 may be extruded from a suitable material, such as polyethylene, polyvinylchloride, silicone, or Kraton, a trademark of Shell Oil Company. The sleeve 16 may be molded or extruded from a suitable material, such as silicone or Kraton, a trademark of Shell Oil Company, or may be made from latex rubber in a suitable manner. The connector 32 and the tip 26 may be molded from a suitable material, such as polyethylene, polyvinylchloride, silicone, or Kraton, a trademark of Shell Oil Company. The formed parts may be assembled in a simplified fashion from dissimilar materials while achieving an improved bond between the sleeve and the tubes and tip, which retain the sleeve in place, although the sleeve and the remaining catheter parts may be constructed from dissimilar materials.

Another embodiment of the catheter of the present invention is illustrated in FIG. 2, in which like reference numerals designate like parts. In this embodiment, the sleeve 16 has an annular inner wall 88, and an annular outer wall 90 joined together at the distal end 18 of the sleeve 16 by a fold 92 of the sleeve, such that the walls 88 and 90 define the cavity 48 between the sleeve walls. Thus, the distal end 18 of the sleeve 16 is closed by the fold 92, while the proximal end 22 of the sleeve 16 may be closed by the bonding means 70. In addition, the cavity 48 intermediate the walls 88 and 90 define a passage for the inflation fluid to the sleeve segment 52 of the outer wall 88 located intermediate the distal end 36 of the second tube 30 and the tip flange 42. Thus, the tube 80 may be connected between the side arm lumen 84 and the cavity 48 at the proximal end 22 of the sleeve 16. Further, the cavity 48 between the sleeve walls 88 and 90 define a passage for the inflation fluid beneath the sleeve portion 58. Thus, in this embodiment, the inflation passage is defined by the sleeve cavity 48, rather than an inflation lumen in the first tube 12.

In use, the sleeve segment 52 of the outer wall 90 is inflated in the patient's bladder by pumping fluid through the tube 80 and the cavity 48 of the sleeve 16. In the event that the sleeve segment 52 is obstructed, such as by inadvertent placement in the patient's urethra, the sleeve portion 58 inflates through the opening 56 of the second wall 30 in order to relieve pressure from the sleeve segment 52 and prevent harm to the patient.

The foregoing detailed description is given for clearness of understanding only, and no unnecessary limitations should be understood therefrom, as modifications will be obvious to those skilled in the art.

I claim:

1. A catheter, comprising:
an elongated inner first tube defining a main lumen;
an elongated annular sleeve of elastic material covering a longitudinal portion of the first tube;
an elongated outer second tube covering a longitudinal portion of said sleeve and having a distal end proximally spaced from a distal end of said sleeve to define an inflatable segment of the sleeve intermediate the distal end of the second tube and the distal end of the sleeve;
means for securing the distal end of the sleeve to the first tube; and
means for establishing communication with said inflatable sleeve segment for inflation thereof.

2. A catheter, comprising:
an elongated inner tube defining a main lumen;
an elongated annular sleeve of elastic material covering a longitudinal portion of the first tube;
a tip secured to a distal end of the inner tube and having a proximally extending annular flange covering and secured to a distal end of the sleeve;
means for retaining said sleeve adjacent the inner tube at a location spaced proximally from said flange to define an inflatable segment of the sleeve intermediate the retaining means and said flange; and
means for establishing communication with said inflatable sleeve segment for inflation thereof.

3. A catheter, comprising:
an elongated inner first tube defining a main lumen;
an elongated annular sleeve of elastic material covering a longitudinal portion of the first tube;
an elongated outer second tube covering a longitudinal portion of said sleeve and having a distal end proximally spaced from a distal end of the sleeve;
a tip secured to a distal end of the first tube and having a proximally extending annular flange covering the distal end of the sleeve, with the distal end of the second tube being spaced from said flange to define an inflatable segment of the sleeve intermediate the distal end of the second tube and said flange; and
means for establishing communication with said inflatable sleeve segment for inflation thereof.

4. The catheter of claim 3 wherein said tip has an opening communicating with the main lumen of the first tube.

5. The catheter of claim 3 wherein said flange is bonded to the distal end of the sleeve.

6. The catheter of claim 3 wherein the distal end of the sleeve is spaced proximally from the distal end of the first tube.

7. The catheter of claim 3 including a connector secured to a proximal end of the first tube.

8. The catheter of claim 7 wherein said connector includes a distally extending annular flange covering a proximal end of the second tube.

9. The catheter of claim 7 wherein said connector includes a distally extending annular flange overlying a proximal end of the sleeve.

10. The catheter of claim 3 wherein said second tube includes an opening overlying a portion of the sleeve proximal said segment to permit inflation of said sleeve portion through the opening.

11. The catheter of claim 3 wherein said sleeve extends substantially the length of the first tube.

12. The catheter of claim 3 wherein said second tube extends substantially the length of the sleeve intermediate the sleeve segment and the proximal end of the sleeve.

13. The catheter of claim 3 wherein said sleeve is bonded to the second tube.

14. The catheter of claim 3 wherein said sleeve is bonded to the first tube adjacent the distal end of the sleeve.

15. The catheter of claim 3 wherein the sleeve is bonded to the first tube proximal said sleeve segment.

16. The catheter of claim 3 wherein said sleeve defines a cavity intermediate the sleeve and said first tube, and including means for closing said cavity at locations proximal and distal said sleeve segment.

17. The catheter of claim 3 wherein the establishing means comprises an inflation lumen in the wall of the first tube, and opening means in the wall of said first tube communicating between the inflation lumen and a cavity beneath said sleeve segment.

18. The catheter of claim 3 wherein said sleeve includes elongated outer and inner walls.

19. The catheter of claim 18 wherein said outer and inner walls are joined at the distal end of the sleeve.

20. The catheter of claim 18 wherein the establishing means comprises a cavity intermediate said inner and outer walls.

21. The catheter of claim 20 wherein said catheter includes a side arm, and in which the establishing means further comprises, means for connecting the side arm to said balloon cavity adjacent a proximal end of the sleeve.

22. The catheter of claim 18 wherein said second tube includes opening means overlying a portion of said outer sleeve wall at a location proximal said sleeve segment to permit inflation of said sleeve portion through the opening means.

* * * * *